US009486417B2

(12) United States Patent
Koch et al.

(10) Patent No.: US 9,486,417 B2

(45) **Date of Patent: *Nov. 8, 2016**

(54) TRANSDERMAL THERAPEUTIC SYSTEM FOR ADMINISTERING LIPOPHILIC AND/OR SPARINGLY SKIN-PERMEABLE ACTIVE SUBSTANCES

(75) Inventors: Andreas Koch, Melsbach (DE); Christoph Schmitz, Rheinbrohl (DE); Rolf Pracht, Höhr-Grenzhausen (DE); Mohammad Sameti, Bonn (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 937 days.

This patent is subject to a terminal disclaimer.

(21) Appl. No.: 13/592,066

(22) Filed: Aug. 22, 2012

(65) Prior Publication Data

US 2012/0316520 A1 Dec. 13, 2012

Related U.S. Application Data

(63) Continuation of application No. 12/083,888, filed as application No. PCT/EP2006/009570 on Oct. 4, 2006, now Pat. No. 8,309,120.

(30) Foreign Application Priority Data

Oct. 21, 2005 (DE) ........................ 10 2005 050 431

(51) Int. Cl.
*A61L 15/44* (2006.01)
*A61K 9/70* (2006.01)

(52) U.S. Cl.
CPC ........... *A61K 9/7053* (2013.01); *A61K 9/7061* (2013.01); *A61K 9/7084* (2013.01)

(58) Field of Classification Search
CPC .... A61K 9/70; A61K 9/7023; A61K 9/7038; A61K 9/7053; A61K 9/7076
USPC .................................................. 424/448, 449
See application file for complete search history.

(56) References Cited

U.S. PATENT DOCUMENTS

| | | | |
|---|---|---|---|
| 4,699,792 A | 10/1987 | Nick et al. | |
| 5,225,199 A * | 7/1993 | Hidaka | A61F 13/02 424/443 |
| 5,980,933 A * | 11/1999 | Bymaster | A61K 9/7061 424/448 |
| 6,019,988 A | 2/2000 | Parab et al. | |
| 6,572,879 B1 * | 6/2003 | Yum | A61K 9/0014 424/449 |
| 8,309,120 B2 * | 11/2012 | Koch et al. | 424/449 |
| 2002/0004065 A1 | 1/2002 | Kanios | |
| 2003/0157155 A1 | 8/2003 | Lipp et al. | |
| 2004/0086552 A1 * | 5/2004 | Klokkers | A61K 9/7053 424/449 |
| 2005/0100588 A1 | 5/2005 | Kartheus et al. | |

FOREIGN PATENT DOCUMENTS

| | | |
|---|---|---|
| CA | 2594065 | 7/2006 |
| DE | 197 01 059 | 7/1998 |
| DE | 100 19 171 | 10/2001 |
| DE | 100 19 311 | 10/2001 |
| DE | 101 28 685 | 12/2002 |
| DE | 102 56 774 | 6/2004 |
| DE | 10 2004 062 614 | 7/2006 |
| EP | 0169364 | 1/1986 |
| WO | WO 00/35456 | 6/2000 |
| WO | WO 01/80859 | 11/2001 |
| WO | WO 2004/052347 | 6/2004 |

OTHER PUBLICATIONS

Farsang, C., J.; *Clin. Basic Cardiol.* 4, (2001), 197.

Gerschlager, W., J.; *Neurol. Neurochem. Psychiatr.*, 5, (2004), 21-24.

Kobayashi, D. et al.; *Biol. Pharm. Bull.*, 16, (1993), 254-258.

* cited by examiner

*Primary Examiner* — Micah-Paul Young

(74) *Attorney, Agent, or Firm* — D. Peter Hochberg; Sean F. Mellino

(57) ABSTRACT

A transdermal therapeutic system for administering lipophilic, poorly water-soluble and/or sparingly skin-permeable pharmaceutical active substances. The active substance is present in a multi-component enhancer system consisting of 4 components and each component of the multi-component enhancer system is selected from a different one of the substance groups: a) terpenes, b) cyclic glucitol ethers, c) medium-chain triglycerides of capric and caprylic acid and/or of linoleic acid; and d) longer-chain alcohols having a chain length of 8 or more carbon atoms.

24 Claims, 3 Drawing Sheets

TRANSDERMAL THERAPEUTIC SYSTEM FOR ADMINISTERING LIPOPHILIC AND/OR SPARINGLY SKIN-PERMEABLE ACTIVE SUBSTANCES

CROSS-REFERENCE TO RELATED APPLICATIONS

This application is a continuation application of co-pending U.S. application Ser. No. 12/083,888 filed on Apr. 21, 2008, which is a National Stage application of International Application No. PCT/EP2006/009570, filed on Oct. 4, 2006, which claims priority of German application number 10 2005 050 431.0, filed on Oct. 21, 2005, all of which are incorporated herein by reference in their entireties.

BACKGROUND OF THE INVENTION

1. Field of the Invention

The present invention relates to a transdermal therapeutic system for the administration of lipophilic, poorly water-soluble and/or sparingly skin-permeable pharmaceutical active substances. More particularly, the present invention relates to a transdermal therapeutic liquid reservoir system for administration of vinpocetine, moxonidine, pergolide or one of their pharmaceutically acceptable salts.

2. Description of the Prior Art

Vinpocetine (ethyl apovincamin-22-oate; 3α16α-apovincaminic acid ethyl ester; ethyl-12-desoxy-12,13-didehydro-vincanol-12-carboxylate) (CAS-No. 42971-09-5) is a pharmaceutical active substance with antioxidant, vasodilating and neuro-protective action which is used for symptomatic treatment of chronic, cerebro-organically caused impairments of performance in the form of impaired memory, impaired concentration, blocking of thought processes, affective disturbances, premature fatigability as well as lack of drive and lack of motivation. At present, this active substance is available on the market only as an oral administration form (tablets) containing 20 mg vinpocetine in the form of its free base—under the brand name CAVINTON®. However, the absorption quota of vinpocetine in a fasting state is only about 6 to 7 percent. Taken during meals, absorption improves by 60 to 100 percent. In both cases, vinpocetine enters the blood stream about half an hour after its administration. With oral administration, its elimination half-life is one to two hours; within eight hours vinpocetine will have been excreted by the body almost completely. In summary, it is to be noted that the bioavailability of orally administered vinpocetine is very poor.

To improve the bioavailability of vinpocetine, a transdermal application with the aid of a transdermal therapeutic system could be taken into consideration. However, the physicochemical properties of vinpocetine are unfavourable for transdermal application. Thus, the partition coefficient log $P_{Octanol/Water}$ of about 3.9 and the poor water-solubility of 0.02 μg/ml at room temperature characterise vinpocetine as a very lipophilic pharmaceutical active substance.

Kobayashi, D. et al. (Biol. Pharm. Bull., 16, (1993) 254-258) describe that is possible to achieve a permeation rate of 6.45 μg/cm$^2$×h with an active substance/enhancer mixture, in the form of a 1% suspension of vinpocetine in a mixture of ethanol and 1-menthol, which was applied in-vitro directly to human full-thickness skin. However, this liquid preparation does not enable a continuous release of active substance, but has to be repeatedly applied in order to achieve an almost constant plasma level of vinpocetine over the day. Therefore, such a liquid administration form is likely to meet with little acceptance among patients.

SUMMARY OF THE PRESENT INVENTION

The first preliminary tests carried out in accordance with the present invention with a view to developing a matrix transdermal therapeutic system for administration of vinpocetine led to transdermal therapeutic systems (TTSs) by means of which a skin flux (permeation rate in steady state) of 0.91 μg/cm$^2$×h could be achieved. In order to adjust the therapeutically required concentration of 2 to 3 ng/ml of vinpocetine in a patient's plasma, a transdermal therapeutic system that is designed for an application period of 24 hours would have to have an area of about 120 cm$^2$. For reasons of patient acceptance, however, the surface area of a transdermal therapeutic system should be kept as small as possible and, if possible, should not exceed 40 cm$^2$, preferably 20 cm$^2$.

The task initially underlying the invention thus consisted in providing a transdermal therapeutic system for administration of vinpocetine which has an acceptable size of not more than 40 cm$^2$. In other words, the task consisted in developing a transdermal therapeutic system for administration of vinpocetine by means of which it is possible to achieve a permeation rate of at least 2.15 μg/cm$^2$×h, preferably at least 5.0×h, which corresponds to a transdermal delivery rate of 2 mg/day. With such a high delivery rate or daily dose, it could be possible to achieve the therapeutically required plasma level of 2 to 3 ng vinpocetine per milliliter of plasma.

Surprisingly, this task is achieved by a liquid reservoir system wherein vinpocetine is present dissolved or suspended in a multi-component enhancer system, said enhancer system consisting of 4 permeation enhancers (=components of the enhancer system) and each component of said enhancer system being selected from a different one of the following substance groups:

a) terpenes
b) cyclic glucitol ethers
c) medium-chain triglycerides of capric and caprylic acid and/or of linoleic acid; and
d) longer-chain alcohols.

In further tests carried out in accordance with the present invention, it emerged, surprisingly, that the enhancer system according to the present description can be advantageously utilised also in connection with other active substances which are similar to vinpocetine in terms of their physico-chemical properties, that is, lipophilic, poorly water-soluble and/or sparingly skin-permeable active substances.

Thus, the present invention relates to transdermal therapeutic systems for administering lipophilic, poorly water-soluble and/or sparingly skin-permeable pharmaceutical active substances.

"Lipophilic", as used in this description, means that the active substance has a high tendency to migrate into a water-immiscible phase. Lipophilic substances are characterized by a high log P value. The log P value is the partition coefficient of a substance between octanol and water: $C_{Octanol}/C_{Water}$.

"Poorly water-soluble" active substance, as used in the present description, are those active substances which possess a solubility in water of less than 0.3%-wt., i.e. substances less than 3 mg of which can be dissolved in one milliliter of water.

The expression "sparingly skin-permeable", as used in the present description, describes active substances whose flux alone, i.e. without permeation enhancers or other measures to increase skin permeation, is too low to be able to achieve the active substance concentration in the plasma necessary in order to attain a therapeutic effect. Generally, those active substances having a molecular weight >("greater than") 500 or a log P of less than −1 or above 4 are regarded as sparingly skin-permeable.

Lipophilic, poorly water-soluble active substances are as a rule characterized by poor bioavailability when administered orally. Transdermal administration of active substances which are poorly bioavailable when administered orally is basically conceivable, it is true, but lipophilic active substances usually also belong to the sparingly or poorly skin-permeable active substances.

DETAILED DESCRIPTION OF THE PRESENT INVENTION

Figure 1:
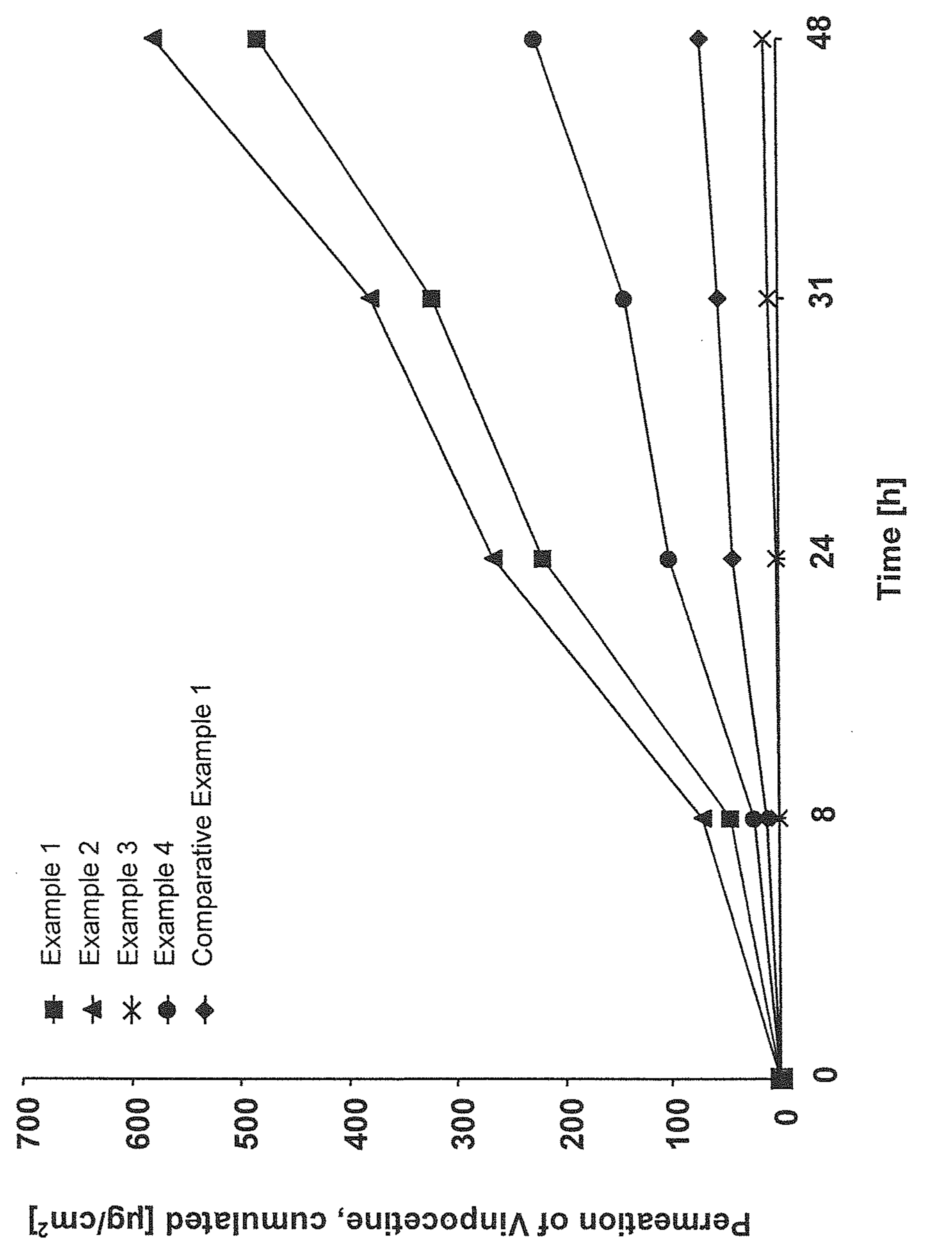
FIG. 1 is a graph showing the accumulated permeation rates of vinpocetine, in accordance with the present invention.

A preferred active substance which by means of the enhancer system of the invention can be administered via the skin with a permeation rate sufficient for therapeutic purposes is moxonidine.

Moxonidine (4-chloro-N-(4,5-dihydro-1H-imidazol-2-yl)-6-methoxy-2-methyl-5-pyrimidinamine; 4-chloro-6-methoxy-2-methyl-5-(2-imidazolin-2-yl)aminopyrimidine) (CAS-No. 75438-57-2) is an imidazole derivative which is recommended for essential hypertonia. It is available as CYNT® film tablets or PHYSIOTENS® film tablets. Moxonidine is gastrointestinally well-absorbed and not metabolised presystemically, so that its bioavailability is about 90%. Moxonidine does, however, have a half-life of only 2 to 3 hours and is excreted substantially via the kidneys. The daily dose necessary is about 0.2 to 0.6 mg; the effective plasma level is around 5.4 ng/ml (according to Farsang, C., J. Clin. Basic Cardiol. 4, (2001), 197). An advantageous effect of moxonidine is that it lowers the increased activity of the sympathetic tone in renal insufficiency. However, compared to the dose for a person with healthy kidneys, in the case of renal insufficiency the maintenance dose of moxonidine must be lowered and/or the dosage interval extended.

Among the clinically useful antihypertensive active substances, moxonidine is the one that has the lowest basicity. At a pH value of 7.4, only about 50% of moxonidine is present in cationic form. Moxonidine is a lipophilic active substance; it has a very low solubility in water, but is soluble up to 100 mM in ethanol or DMSO. The water solubility of moxonidine (base) is 1.36 mg/ml at 22° C. Its partition coefficient log $P_{Octanol/Water}$ is −1.3. These two values characterise moxonidine (the free base) as a poorly water-soluble and sparingly skin-permeable substance.

A further active substance that can be administered via the skin with the aid of the inventive enhancer system at a permeation rate sufficient for therapeutic purposes is pergolide.

Pergolide ((8β β-8-[(methylthio)methyl]-6-propyl-ergoline, D-6-n-propyl-8 β-methyl-mercaptomethyl-ergoline) (CAS-No. 66104-22-1) is a semisynthetic ergoline with strong dopamine(D)-2-agonistic and a lower D-1-receptor-agonistic action which is approved for the treatment of Parkinson's disease. Although the chemical structure of pergolide is different from that of dopamine, it does act on the same binding sites as dopamine. Moreover, it does also have an effect in lowering the prolactin concentration in the plasma. The plasma half-life of pergolide after oral administration is 27 hours. The daily dose is about 5 mg (Gerschlager, W., J. Neurol. Neurochem. Psychiatr., 5, (2004), 21-24). The water-solubility of pergolide (base) is 0.021 μg/ml at 22° C. Its partition coefficient log $P_{Octanol/Water}$ is about 4.02. These two values characterise the pergolide base as a very poorly water-soluble and sparingly skin-permeable substance.

Because of their ionic character, also the pharmacologically acceptable salts of vinpocetine, moxonidine and pergolide are counted among the sparingly skin-permeable substances, even though their water-solubility is higher than that of vinpocetine, moxonidine or pergolide, respectively. Therefore, the pharmacologically acceptable salts of vinpocetine, the pharmacologically acceptable salts of moxonidine and the pharmacologically acceptable salts of pergolide also belong to the substances or active substances that can be transdermally administered with the inventive multi-component enhancer system at a permeation rate that is sufficient for therapeutic purposes. Examples of known salts of the active substances mentioned are moxonidine hydrochloride and pergolide mesylate.

Transdermal therapeutical liquid reservoir systems as such, wherein a—generally liquid—active substance preparation is contained in a bag formed of a release-controlling membrane and a—preferably active substance-impermeable—are known to those skilled in the art. In these systems, pharmaceutically acceptable and skin-tolerated organic solvents serve as carrier medium whose viscosity can be adjusted with suitable auxiliary substances (e.g. mineral oils) to meet the respective technological requirements. Ideally, the solvents used also possess properties promoting the permeation of the active substance through the patient's skin. However, substances promoting the permeation of the active substance, so-called enhancers, may be added to the solvent. In addition, the liquid reservoir systems comprise a pressure-sensitive adhesive layer by which the system is attached to the patient's skin.

In the liquid reservoir system according to the invention, the lipophilic, poorly water-soluble and/or sparingly skin-permeable active substance is present in a multi-component enhancer system in dispersed or suspended form, said enhancer system consisting of four enhancers which increase the permeation of the active substance. Each of the enhancers of said multi-component enhancer system comes from a different group of substances. The substance groups from which the enhancers are selected are:

a) terpenes;

b) cyclic glucitol ethers;

c) triglycerides of capric and caprylic acid and/or of linoleic acid; and d) longer-chain alcohols.

Terpenes can be derived from isoprene or from isopentenyl units, which means that the number of the carbon atoms contained in their skeletal structure can be divided by 5. According to the number of isoprene residues, a distinction is drawn between monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$) and polyterpenes. Furthermore, there also are naturally occurring terpenes whose structure is not in keeping with the isoprene rule. The terpenes are a heterogenic group of compounds which, due to their different functional groups, can be assigned to different substance groups, so that terpenes are considered to include both hydrocarbons as well as the alcohols, ketones, aldehydes and esters that are derived therefrom.

In accordance with the invention, preference is given to monoterpenes, that is, terpenes made up of two isoprene units. Examples of monoterpenes are pinene, nerol, citral, camphor, menthol, carvacrol, thymol and limonene.

The monoterpenes can be divided into acyclic, monocyclic and bicyclic monoterpenes. The acyclic monoterpenes include, for example, myrcene, ocimene and cosmene. Especially preferred are, in accordance with the invention, the monocyclic monoterpenes which have a cyclohexane skeleton and can thus be derived from p-menthane.

Mostly, the monocyclic monoterpenes with cyclohexane skeleton are in turn divided according to their secondary allocation to substance groups. Especially preferred are alcoholic monocyclic monoterpenes with cyclohexane skeleton, especially eucalyptol.

Particularly suitable as the cyclic glucitol ether is dimethyl isosorbide. Glucitol, also called sorbitol, is the sugar alcohol of glucose.

Amongst the triglycerides of capric and caprylic acid and/or of linoleic acid, those are used with preference which are sold under the brand name MIGLYOL®, preferably MIGLYOL® 808, MIGLYOL® 810 and MIGLYOL® 812, with MIGLYOL® 812 being particularly preferred.

Used as the longer-chain alcohols are those alcohols having a chain length of at least 8 carbon atoms, preferably at least 12 carbon atoms, preferably monohydric alcohols, especially preferably 1-dodecanol.

In a preferred embodiment, the components of the multi-component enhancer system are present in a mixing ratio wherein the proportion of the component used in the lowest dose is at least 10%-wt. and the proportion of the most highly dosed component is maximally 40%-wt., each relative to the overall weight of the multi-component enhancer system.

The most highly preferred multi-component enhancer system is made up as follows:

a) 25%-wt. eucalyptol as terpene;

b) 25%-wt. dimethyl isosorbide as cyclic glucitol ether;

c) 35%-wt. miglyol 812 as medium-chain triglyceride of caprylic and capric acid; and d) 15%-wt. 1-dodecanol as longer-chain alcohol with a chain length of 12 carbon atoms or more.

The proportion of active substance in the active substance-containing preparation amounts to 0.1 to 50%-wt., preferably 5 to 25%-wt.

The preparation contained in the liquid reservoir thus comprises the active substance, which may be present in the multi-component enhancer system in dissolved, dispersed or suspended form. In addition, the active substance preparation may contain further substances by which the release of active substance—in the sense of a retarded release—can be controlled. Absorption agents are an example of those substances.

The absorption agents may be selected from the group containing cyclodextrins, polyvinyl pyrrolidone and cellulose derivatives.

The active substance preparation may additionally contain viscosity-increasing auxiliary substances that do not have a release-controlling function. The viscosity-increasing auxiliary substance is preferably selected from the group consisting of finely dispersed silicon dioxide, preferably AEROSIL R974®, polyacrylic acids, e.g. CARBOPOL 934®, mineral oils, wool waxes and high-molecular polyethylene glycols. An example of a preferred polyethylene glycol is CARBOWAX 1000®. The active substance preparation may be present in the liquid reservoir as a solution, dispersion, suspension, paste or gel.

In the transdermal therapeutic system according to the present invention, the release of the active substance and of the enhancers from the liquid reservoir system can be controlled via:

the type of control membrane used, for example via its chemical composition and/or the pore size;

the type of the pressure-sensitive adhesive layer used below the control membrane, by which the system is attached to the skin, for example via the chemical composition and/or the layer thickness of said adhesive layer;

a retarded delivery, achieved by the use of absorption agents in the liquid reservoir, for example of cyclodextrins, polyvinyl pyrrolidones or cellulose derivatives.

As control membrane, microporous polymer films may be utilised which are produced with a defined pore size and are made of polyethylene, polypropylene, polyurethane, copolymers of ethylene and vinyl acetate, and silicones. These polymer films are suitable provided that they are resistant to the substances contained in the active substance preparation.

As pressure-sensitive adhesives which have properties that control the release of the pharmaceutical active substance, and which are attached below the control membrane for fixing the system on the skin, those pressure-sensitive adhesives are preferred as are based on copolymers of ethylene and vinyl acetate, in combination with adhesive resins and additives. With these pressure-sensitive adhesives, the penetrability or permeability of the pressure-sensitive adhesive layer can be adjusted via the ratio of ethylene to vinyl acetate. Also preferred are pressure-sensitive adhesives based on silicones since these are permeable to most of the active substances and auxiliary substances, as well as pressure-sensitive adhesives based on poly(meth) acrylates, and pressure-sensitive adhesives based on polyisobutylenes.

In the following, the invention will be illustrated in more detail by means of examples; these examples should, however, not be understood as being the only combinations for which protection is sought by the present application.

Examples 1 to 4

To prepare the pressure-sensitive adhesive liquid reservoir systems as specified in more detail in Table 1, first, an active substance-free polyacrylate adhesive solution of the DUROTAK® 1050 type (National Starch, Antwerp) or a copolymer of ethylene and vinyl acetate with addition of an adhesive resin based on colophony (FORAL® 85 B) is spread with a wet-layer thickness of 300 μm on a siliconised polyethylene terephthalate film with the aid of a doctor knife.

Subsequently, the solvents were withdrawn by drying the coated film for half an hour at 50° C. in a drying cupboard with a waste air duct. The solvent-free and active substance-free adhesive film was then covered with a 35-μm-thick polyurethane film (OPRAFLEX®, Lohmann) or with a polypropylene film by laminating, said film later serving as the control membrane. Onto this control membrane was placed a polyester film (SCOTCHPAK® No. 1220, 3M) and sealed to form bags having a round reservoir of a diameter of 25 mm, using a special sealing mask heated by a commercial electric iron.

Via an existing orifice leading to the reservoir, the respective vinpocetine/enhancer mixture—the enhancer components of which had previously been mixed together in their respective weight percentages—was filled into the reservoir using a syringe. The amount of vinpocetine was 10%-wt., relative to the overall weight of the active substance/enhancer mixture. Following the filling of the reservoir, the filling orifice was welded using an electric iron, so that a completely closed and storage-stable liquid reservoir system was obtained Comparative Example 1

A matrix transdermal therapeutic system was prepared as a reference for the vinpocetine-containing liquid reservoir systems by dissolving OPPANOL® B 10 and OPPANOL® B 100, medium-molecular and high-molecular polyisobutylenes from BASF in different mixing ratios in special boiling point gasoline of type 80/110, and subsequently dispersing therein 2%-wt. vinpocetine and 17%-wt. lauryl lactate as enhancers. By stirring for 30 minutes, a homogenous distribution of the active substance crystals in the adhesive solution was achieved. This was followed by degassing the dispersion in an ultrasound bath for 10 to 15 minutes.

To produce the self-adhesive, active substance-containing film, a siliconised polyethylene terephthalate film was coated with the active substance-containing adhesive material in a wet layer thickness of 400 μm with the aid of a manual doctor-knife. The air from around the adhesive coating was exhausted for 20 minutes at room temperature, before the coating was dried for 10 minutes at 70° C.

The solvent-free, active substance-containing and self-adhesive coating was subsequently covered with a 15-μm-thick polyethylene terephthalate film by laminating.

Examples 5 and 6

Pressure-sensitive adhesive liquid reservoir systems for administration of moxonidine were produced in accordance with the method indicated for Examples 1 to 4, by spreading and drying an active substance-free polyacrylate adhesive solution and subsequently covering same with a 35-μm-thick polyurethane film (OPRAFLEX®, Lohmann), as the control membrane, by laminating. A polyester film was placed on the control membrane and sealed with the special sealing mask to form bags which had a round reservoir of a diameter of 25 mm.

Via an existing orifice leading to the reservoir, the respective active substance/enhancer mixture containing 10%-wt. moxonidine was filled by a syringe into the reservoir, which was subsequently sealed, so that a completely closed and storage-stable liquid reservoir system was obtained.

Comparative Example 2

As comparative example for the moxonidine-containing liquid reservoir systems, a matrix transdermal therapeutic system was produced that constituted a transdermal therapeutic system with permeation enhancer which was already optimised for the transdermal administration of moxonidine.

Examples 7 and 8

Pressure-sensitive adhesive liquid reservoir systems for the administration of pergolide were produced in accordance with the method indicated for Examples 1 to 4 by spreading and drying an active substance-free polyacrylate adhesive solution and thereafter covering same with a 35-μm-thick polyurethane film (OPRAFLEX®, Lohmann), which serves as a control membrane, by laminating. A polyester film was placed on the control membrane and sealed with the special sealing mask to form bags which had a round reservoir of a diameter of 25 mm.

Via an existing orifice leading to the reservoir, the respective active substance/enhancer mixture containing 10%-wt. pergolide was filled by a syringe into the reservoir, which was subsequently sealed, so that a completely closed and storage-stable liquid reservoir system was obtained.

Comparative Example 3

As comparative example for the pergolide-containing liquid reservoir systems, a matrix transdermal therapeutic system was produced that constituted a transdermal therapeutic system with permeation enhancer which was already optimised for the transdermal administration of pergolide.

Determination of the permeation rates: The permeation rates of the aforementioned systems were determined in the in-vitro diffusion model of "human epidermis" with the aid of modified Franz diffusion cells. In all of the cases, phosphate buffer (pH 5.5) with an addition of 0.1% $NaN_3$ was used as the preservative agent.

The accumulated permeation rates of vinpocetine are shown in FIG. 1; the individual measurement points represent the mean value of three individual measurements. The results of the tests on the permeation of vinpocetine are summarised in Table 1.

TABLE 1

Comparison of the permeation rates of vinpocetine achieved with different transdermal therapeutic systems

| System | Control membrane | Pressure-sensitive adhesive | Enhancer component(s) | % by weight of the components in the enhancer mixture | In vitro-skin flux [μg/cm$^2$xh] |
|---|---|---|---|---|---|
| Example 1 | Polyurethane | Polyacrylate | Miglyol type 812<br>dimethyl isosorbide<br>Eucalyptol<br>1-Dodecanol | 35<br>25<br>25<br>15 | 10.9 |

TABLE 1-continued

Comparison of the permeation rates of vinpocetine achieved with different transdermal therapeutic systems

| System | Control membrane | Pressure-sensitive adhesive | Enhancer component(s) | % by weight of the components in the enhancer mixture | In vitro-skin flux [μg/cm²xh] |
|---|---|---|---|---|---|
| Example 2 | Polypropylene | Ethylene-vinyl acetate copolymer with addition of a colophony-based adhesive resin | Miglyol type 812<br>Dimethyl isosorbide<br>Eucalyptol<br>1-Dodecanol | 35<br>25<br>25<br>15 | 13.0 |
| Example 3 | Polyurethane | Polyacrylate | Miglyol type 812<br>Dimethyl isosorbide<br>Ethanol<br>1-Dodecanol | 35<br>25<br>25<br>15 | 0.426 |
| Example 4 | Polyurethane | Polyacrylate | Lauryl lactate | 100 | 1.16 |
| Comparative Example 1 | N/A | Polyisobutylene | Lauryl lactate | 17 | 1.10 |

For a transdermal therapeutic system according to Example 1, for example, it follows from Table 1 that in accordance with the relation $Q_{SS}=J_{SS}\times A/Cl$ a transdermal therapeutic system having a release surface of 10 $cm^2$ would be sufficient to achieve a vinpocetine plasma level of 2.5 ng/ml, the quantities $Q_{SS}$, $J_{SS}$, A and Cl having the following meanings:

$Q_{SS}$=steady state plasma level, in ng/ml;

$J_{SS}$=in-vitro skin flux, in μg/$cm^2$×h;

A=effective release surface area of the system, in $cm^2$; and

Cl=Clearance (purification rate, amount of plasma per unit of time of a certain active substance) in 1/h; value for vinpocetine taken from Kobayashi, D. et al., Biol. Pharm. Bull., 16, (1993), 254-258).

Figure 2:
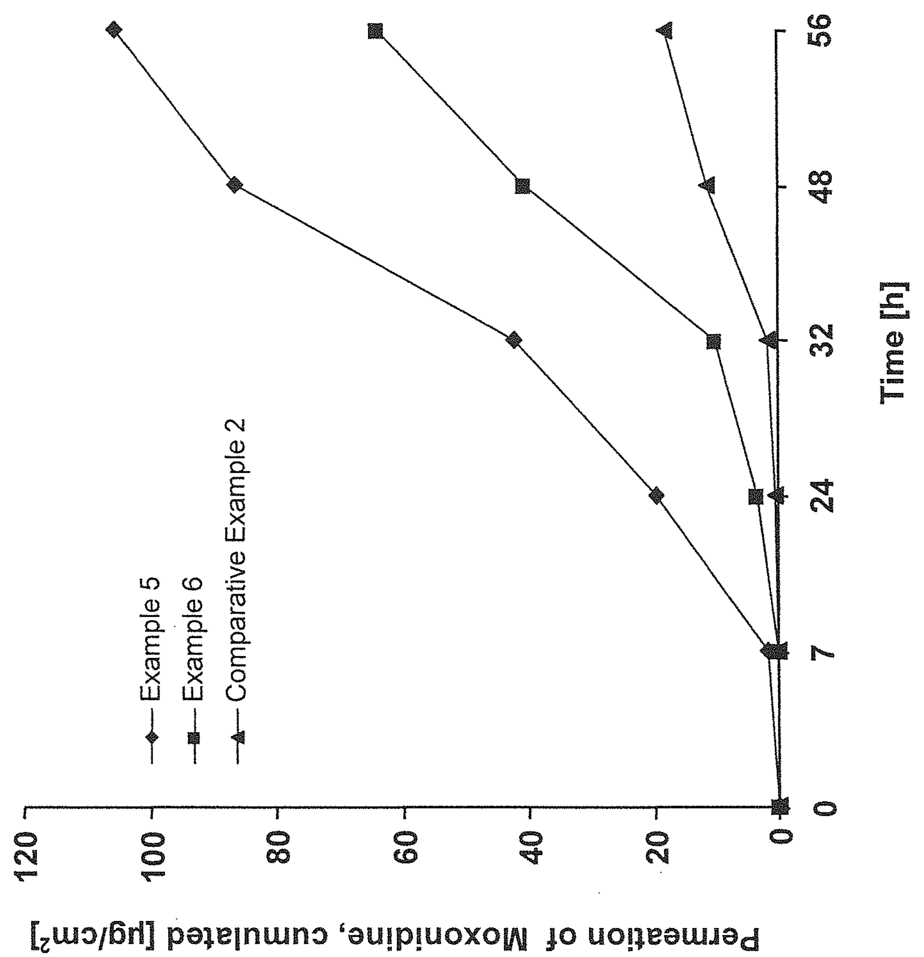
FIG. 2 is a graph showing the cumulated permeation rates of moxonidine, in accordance with the present invention.

The cumulated permeation rates of moxonidine are shown in FIG. 2; the individual measurement points represent the mean value of three individual measurements. The results of the tests on the permeation of moxonidine are summarised in Table 2.

As shown by a comparison between the experimental results relating to the transdermal release of moxonidine, a liquid reservoir system according to Example 6 leads to permeation rates which are about 60% below those obtained with a liquid reservoir system according to Example 5. FIG. 2 illustrates the synergistic effect of the four enhancer components contained in a liquid reservoir system according to Example 5.

TABLE 2

Comparison of the permeation rates of moxonidine achieved with different transdermal therapeutic systems

| System | Control membrane | Pressure-sensitive adhesive | Enhancer component(s) | % by weight of the components in the enhancer mixture | In vitro-skin flux [μg/cm²xh] |
|---|---|---|---|---|---|
| Example 5 | Poly-urethane | Polyacrylate | Miglyol type 812<br>Dimethyl isosorbide<br>Eucalyptol<br>n-Dodecanol | 35<br>25<br>25<br>15 | 2.79 |
| Example 6 | Poly-urethane | Polyacrylate | Lauryl lactate<br>Oleic acid<br>Eucalyptol<br>Menthol | 35<br>25<br>25<br>15 | 1.56 |
| Comparative Example 2 | | | | | 0.447 |

Figure 3:
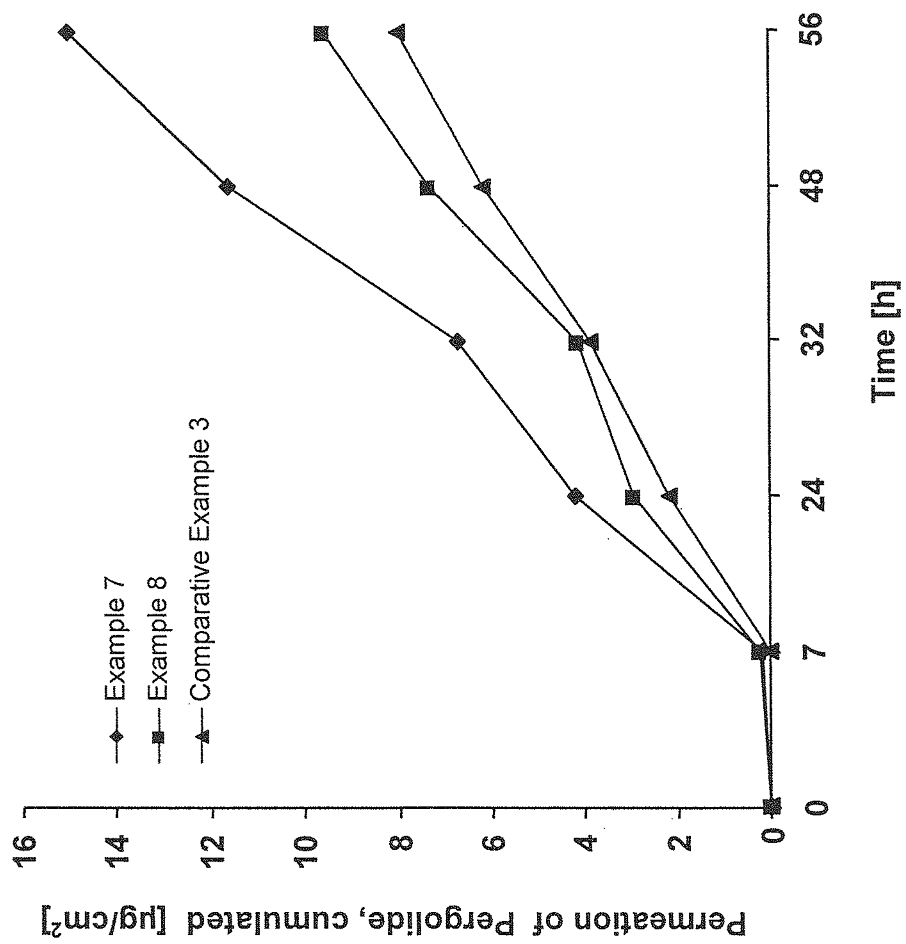
FIG. 3 is a graph showing the cumulated permeation rates of pergolide, in accordance with the present invention.

The cumulated permeation rates of pergolide are shown in FIG. 3; the individual measurement points represent the mean value of three individual measurements. The results of the tests on the permeation of pergolide are summarised in Table 3.

As shown by a comparison between the experimental results relating to the transdermal release of pergolide, a liquid reservoir system according to Example 8 leads to permeation rates which are about 60% below those obtained with a liquid reservoir system according to Example 7, which contains only a single permeation enhancer. FIG. 3 illustrates the synergistic effect of the four enhancer components contained in a liquid reservoir system according to Example 7 as compared to the mono-enhancer system eucalyptol (Example 8).

TABLE 3

Comparison of the permeation rates of pergolide achieved with different transdermal therapeutic systems

| System | Control membrane | Pressure-sensitive adhesive | Enhancer component(s) | % by weight of the components in the enhancer mixture | In vitro-skin flux [μg/cm²xh] |
|---|---|---|---|---|---|
| Example 7 | Polyurethane | Polyacrylate | Miglyol type 812<br>Dimethyl isosorbide<br>Eucalyptol<br>n-Dodecanol | 35<br>25<br>25<br>15 | 0.309 |
| Example 8 | Polyurethane | Polyacrylate | Eucalyptol | 100 | 0.185 |
| Comparative Example 3 | | | | | 0.165 |

As is shown by a comparison of the experimental results, the liquid reservoir systems according to the invention lead to permeation rates which are clearly higher than those obtainable with a matrix transdermal therapeutic system and which are clearly above the set target.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A transdermal therapeutic system for administering in varying sizes of doses a lipophilic, poorly water-soluble and sparingly skin-permeable active substance, wherein the active substance possesses a solubility in water of less than 0.3%-wt. and is present in a form selected from the group consisting of a dissolved form and a suspended form in a multi-component enhancer system for forming an active substance-containing preparation, said enhancer system consisting of 4 enhancer-components and each component of said multi-component enhancer system being selected from a different one of the substance groups:

a) terpenes in an amount of 25%-wt.;

b) cyclic glucitol ethers in an amount of 25%-wt.;

c) medium-chain triglycerides of capric and caprylic acid and/or of linoleic acid in an amount of 35%-wt.; and d) longer-chain alcohols having a chain length of 8 or more carbon atoms in an amount of 15%-wt.

2. The transdermal therapeutic system according to claim 1, wherein the enhancer-components are present in a mixing ratio wherein the proportion of the component used in the lowest dose is at least 10%-wt. and the proportion of the most highly dosed component is maximally 40%-wt., relative to the multi-component enhancer system.

3. The transdermal therapeutic system according to claim 1, wherein the active substance is selected from the group consisting of vinpocetine, moxonidine, pergolide and the pharmaceutically acceptable salts of vinpocetine, moxonidine and pergolide.

4. The transdermal therapeutic system according to claim 1, wherein the content of said active substance is 0.1 to 50%-wt. relative to the active substance-containing preparation.

5. The transdermal therapeutic system according to claim 1, wherein said transdermal therapeutic system further comprises a liquid reservoir system, and wherein said active substance and all of the enhancer-components are present in said liquid reservoir system.

6. The transdermal therapeutic system according to claim 5, wherein said liquid reservoir system comprises a control membrane for controlling the release of the enhancer-components and of the active substance.

7. The transdermal therapeutic system according to claim 6, wherein said control membrane consists of a polymer selected from the group consisting of polyethylenes, polypropylenes, silicones, polyurethanes and copolymers of ethylene and vinyl acetate.

8. The transdermal therapeutic system according to claim 6, wherein said liquid reservoir system comprises a pressure-sensitive adhesive layer located below the control membrane, wherein the pressure-sensitive adhesive of said pressure-sensitive adhesive layer is selected from the group consisting of silicones, acrylates, polyisobutylenes and copolymers of ethylene and vinyl acetate, and wherein the addition of adhesive resins renders said copolymers of ethylene and vinyl acetate adhesive.

9. The transdermal therapeutic system according to claim 8, wherein said pressure-sensitive adhesive layer located below the control membrane controls the release of the active substance, wherein said control membrane exerts a controlling effect by the layer thickness.

10. The transdermal therapeutic system according to claim 8, wherein adhesive resins are added to said pressure-sensitive adhesive layer based on copolymers of ethylene and vinyl acetate, and pressure-sensitive adhesive layer based on copolymer of ethylene and vinyl acetate with the addition of adhesive resins exerts a controlling effect by the ratio of ethylene to vinyl acetate.

11. The transdermal therapeutic system according to claim 1, wherein said active substance-containing preparation contains additional auxiliary substances in the form of thickening agents, wherein said additional auxiliary substances are selected from the group consisting of mineral oils, wool waxes, polyacrylic acids, high-molecular polyethylene glycols and finely dispersed silicon dioxide.

12. The transdermal therapeutic system according to claim 1, wherein said active substance-containing preparation is present in a form selected from the group consisting of a solution, a dispersion, a suspension, a paste and a gel.

13. The transdermal therapeutic system according to claim 1, wherein said active substance-containing preparation additionally contains control elements in the form of a retarded release, said control elements being selected from the group consisting of cyclodextrins, polyvinyl pyrrolidones and cellulose derivatives.

14. The transdermal therapeutic system according to claim 1, wherein said multi-component enhancer system comprises:

a) eucalyptol, b) dimethyl isosorbide, c) triglycerides of capric and caprylic acid and/or of linoleic acid, and d) 1 dodecanol.

15. The transdermal therapeutic system according to claim 4, wherein the content of said active substance is 5.0 to 25.0%-wt. relative to the active substance-containing preparation.

16. The transdermal therapeutic system according to claim 1, wherein the active substance is vinpocetine or a pharmaceutically acceptable salt thereof.

17. The transdermal therapeutic system according to claim 1, wherein the active substance is moxonidine or a pharmaceutically acceptable salt thereof.

18. The transdermal therapeutic system according to claim 1, wherein the active substance is selected from the group consisting of vinpocetine, moxonidine, pergolide, pharmaceutically acceptable salts of vinpocetine, pharmaceutically acceptable salts of moxonidine and pharmaceutically acceptable salts of pergolide, and wherein said multi-component enhancer system comprises:

(a) an alcoholic monocyclic monoterpene having a cyclohexane skeleton as said terpene;

(b) dimethyl isosorbide as said cyclic glucitol ether;

(c) medium-chain triglycerides of capric and caprylic acid and/or of linoleic acid; and (d) 1-dodecanol as said longer-chain alcohol.

19. The transdermal therapeutic system according to claim 18, wherein said alcoholic monocyclic monoterpene is eucalyptol.

20. The transdermal therapeutic system according to claim 18, wherein the active substance is vinpocetine or a pharmaceutically acceptable salt thereof.

21. The transdermal therapeutic system according to claim 18, wherein the active substance is moxonidine or a pharmaceutically acceptable salt thereof.

22. The transdermal therapeutic system according to claim 1, wherein said active substance has a log P value of above 4, said log P value being the partition coefficient of a substance between octanol and water.

23. The transdermal therapeutic system according to claim 1, wherein said active substance has a log P value of less than −1, said log P value being the partition coefficient of a substance between octanol and water.

24. A transdermal therapeutic system for administering in varying sizes of doses a lipophilic, poorly water-soluble and sparingly skin-permeable active substance, wherein the active substance possesses a solubility in water of less than 0.3%-wt. and is present in a form selected from the group consisting of a dissolved form and a suspended form in a multi-component enhancer system for forming an active substance-containing preparation, said enhancer system comprising 4 enhancer-components and each component of said multi-component enhancer system being selected from a different one of the substance groups:

a) terpenes in an amount of 25%-wt.;

b) cyclic glucitol ethers in an amount of 25%-wt.;

c) medium-chain triglycerides of capric and caprylic acid and/or of linoleic acid in an amount of 35%-wt.; and d) longer-chain alcohols having a chain length of 8 or more carbon atoms in an amount of 15%-wt.

* * * * *